(12) United States Patent
Nix et al.

(10) Patent No.: US 10,347,382 B2
(45) Date of Patent: Jul. 9, 2019

(54) METHODS AND APPARATUS FOR GEOGRAPHY-BASED ANTIMICROBIAL RESISTANCE TRACKING

(71) Applicant: athenahealth, Inc., Watertown, MA (US)

(72) Inventors: Robert Nix, San Francisco, CA (US); Shayne Guiliano, Hillsborough, NC (US); Anne Meneghetti, San Francisco, CA (US); Peter Hung, Los Altos, CA (US); Nathan Wilkinson, Raleigh, NC (US); Abbe Don, San Francisco, CA (US); Alexander C. Jergensen, Durham, NC (US); Jeremy Magid, Durham, NC (US)

(73) Assignee: athenahealth, Inc., Watertown, MA (US)

( * ) Notice: Subject to any disclaimer, the term of this patent is extended or adjusted under 35 U.S.C. 154(b) by 197 days.

(21) Appl. No.: 14/500,596

(22) Filed: Sep. 29, 2014

(65) Prior Publication Data
US 2016/0092657 A1 Mar. 31, 2016

(51) Int. Cl.
G16H 70/60 (2018.01)
G06F 19/00 (2018.01)
G16H 50/80 (2018.01)

(52) U.S. Cl.
CPC .......... *G16H 50/80* (2018.01); *G06F 19/324* (2013.01); *G16H 70/60* (2018.01); *Y02A 90/24* (2018.01); *Y02A 90/26* (2018.01)

(58) Field of Classification Search
CPC .................................................. G06F 19/3493
See application file for complete search history.

(56) References Cited

U.S. PATENT DOCUMENTS

| 4,858,121 A | * | 8/1989 | Barber ............... G06F 19/328 235/380 |
| 5,253,164 A | * | 10/1993 | Holloway ............ G06Q 40/02 705/2 |
| 6,000,828 A | * | 12/1999 | Leet .................... G06F 19/325 705/2 |

(Continued)

OTHER PUBLICATIONS

U.S. Appl. No. 60/203,315, Ross, filed May 10, 2000.
(Continued)

*Primary Examiner* — Elaine Gort
*Assistant Examiner* — Rachelle L Reichert
(74) *Attorney, Agent, or Firm* — Fish & Richardson P.C.

(57) ABSTRACT

Methods and apparatus for tracking antimicrobial resistance based on geography. An application server receives a query from a client application to provide antimicrobial resistance data for a geographic location. The application server determines a geographic region based, at least in part, on the geographic location included in the query, and antimicrobial data for samples collected from patients residing in the geographic region are retrieved from at least one health information datastore of a health information system. The retrieved antimicrobial data comprises information describing antimicrobial resistance of an infectious organism detected in the biological samples to at least one antimicrobial agent, and is transmitted to a client device on which the client application that issued the query is executing.

21 Claims, 7 Drawing Sheets

(56) References Cited

U.S. PATENT DOCUMENTS

| | | | | |
|---|---|---|---|---|
| 6,076,066 | A * | 6/2000 | DiRienzo | G06F 3/0481 705/2 |
| 6,208,973 | B1 * | 3/2001 | Boyer | G06Q 20/02 705/2 |
| 6,341,265 | B1 * | 1/2002 | Provost | G06Q 40/02 705/2 |
| 6,343,271 | B1 * | 1/2002 | Peterson | G06Q 40/02 705/2 |
| 7,016,856 | B1 * | 3/2006 | Wiggins | G06F 19/328 705/2 |
| 7,447,988 | B2 * | 11/2008 | Ross | G06F 19/322 715/221 |
| 7,809,585 | B1 * | 10/2010 | Ghouri | G06F 19/326 705/2 |
| 2002/0032584 | A1 * | 3/2002 | Doctor | G06Q 10/10 705/3 |
| 2002/0107641 | A1 * | 8/2002 | Schaeffer | G06F 19/345 702/19 |
| 2004/0078146 | A1 * | 4/2004 | Lombardo | G06F 19/3493 702/19 |
| 2004/0260666 | A1 * | 12/2004 | Pestotnik | G06Q 50/22 706/46 |
| 2006/0155663 | A1 * | 7/2006 | Byington | G06F 19/325 706/47 |
| 2006/0229822 | A1 * | 10/2006 | Theobald | G06Q 50/24 702/19 |
| 2007/0106626 | A1 * | 5/2007 | Mundie | G06N 99/005 706/20 |
| 2007/0174252 | A1 * | 7/2007 | Rawlings | G06F 19/3487 |
| 2008/0091471 | A1 * | 4/2008 | Michon | G06F 19/3443 705/3 |
| 2008/0206767 | A1 * | 8/2008 | Kreiswirth | C12Q 1/689 435/6.15 |
| 2008/0210748 | A1 * | 9/2008 | Jung | G01N 33/5302 235/375 |
| 2009/0100007 | A1 * | 4/2009 | Campbell | G06F 17/3087 |
| 2009/0132929 | A1 * | 5/2009 | Reed, Jr. | G06F 17/3087 715/739 |
| 2009/0299767 | A1 * | 12/2009 | Michon | G06F 19/3443 705/3 |
| 2009/0319518 | A1 * | 12/2009 | Koudas | G06F 17/30864 |
| 2010/0082301 | A1 * | 4/2010 | Skibiski | H04L 41/12 702/188 |
| 2010/0332475 | A1 * | 12/2010 | Birdwell | G06F 17/30333 707/737 |
| 2011/0020785 | A1 * | 1/2011 | Lowery, Jr. | G06F 19/3418 435/5 |
| 2011/0040797 | A1 * | 2/2011 | Haskell | G06Q 10/10 707/797 |
| 2011/0161096 | A1 * | 6/2011 | Buehler | G06F 17/30241 705/2 |
| 2011/0238316 | A1 * | 9/2011 | Ecker | C07H 21/04 702/19 |
| 2013/0031041 | A1 * | 1/2013 | Maciejewski | G06Q 10/10 706/46 |
| 2013/0268292 | A1 * | 10/2013 | Kim | G06F 19/3418 705/2 |
| 2013/0325502 | A1 * | 12/2013 | Robicsek | G06Q 10/04 705/3 |
| 2013/0339053 | A1 * | 12/2013 | Jacobs | G06F 19/3443 705/3 |

OTHER PUBLICATIONS

Civil Action No. 1:13-cv-10794-IT, athenahealth, Inc.'s Opening Claim Construction Brief, dated Jun. 27, 2014, filed Jun. 27, 2014. 23 pages.

Civil Action No. 1:13-cv-10794-IT, athenahealth, Inc.'s Proposed Claim Constructions and Support, dated Apr. 25, 2014, filed Apr. 25, 2014. 7 pages.

Civil Action No. 1:13-cv-10794-IT, athenahealth, Inc.'s Preliminary Identification of Claim Terms to be Construed, dated Apr. 11, 2014, filed Apr. 11, 2014. 3 pages.

Civil Action No. 1:13-cv-10794-IT, athenahealth, Inc.'s Replacement Claim Construction Reply Brief, dated Sep. 5, 2014, filed Sep. 10, 2014. 15 pages.

Civil Action No. 1:13-cv-10794-IT, CareCloud Corporation's Claim Construction Sur-Reply Brief, dated Oct. 6, 2014, filed Oct. 6, 2014. 16 pages.

Civil Action No. 1:13-cv-10794-IT, CareCloud Corporation's Identification of Claim Terms/Phrases for Construction, dated Apr. 11, 2014, filed Apr. 11, 2014. 4 pages.

Civil Action No. 1:13-cv-10794-IT, CareCloud Corporation's Preliminary Invalidity Contentions, dated Jan. 10, 2014, filed Jan. 10, 2014. 106 pages.

Civil Action No. 1:13-cv-10794-IT, CareCloud Corporation's Responsive Claim Construction Brief, dated Aug. 1, 2014, filed Aug. 1, 2014. 24 pages.

Civil Action No. 1:13-cv-10794-IT, Declaration of Chi Cheung in Support of CareCloud Corporation's Responsive Claim Construction Brief, .dated Aug. 1, 2014, filed Aug. 1, 2014. 40 pages.

Civil Action No. 1:11-cv-11260-GAO, "Advanced Billing Features," webpage found at http://web.archive.org/web/19981202203523/http://www.medicalmanager.com/v9/004.htm. 6 pages.

Civil Action No. 1:11-cv-11260-GAO, "Customization," webpage found at http://web.archive.org/web/19981205131953/http://www.medicalmanager.com/v9/007.htm. 3 pages.

Civil Action No. 1:11-cv-11260-GAO, "Electronic Communications," webpage found at http://web.archive.org/web/19981206025311/http://web.medicalmanager.com/v9/003.htm. 4 pages.

Civil Action No. 1:11-cv-11260-GAO, "Executive Summary," webpage found at http://web.archive.org/web/19990221040230/http://www.medicalmanager.com/v9/summary.htm. 6 pages.

Civil Action No. 1:11-cv-11260-GAO, "Introduction," webpage found at http://web.archive.org/web/19981205002805/http://www.medicalmanager.com/v9/intro.htm. 1 page.

Civil Action No. 1:11-cv-11260-GAO, "Patient Entry and Billing Cycles," webpage found at http://web.archive.org/web/1998120600426/http://www.medicalmanager.com/v9/002.htm. 6 pages.

Civil Action No. 1:11-cv-11260-GAO, Corrected Request for Ex Parte Reexamination of U.S. Pat. No. 6,343,271. Nov. 14, 2011. 1487 pages.

Civil Action No. 1:11-cv-11260-GAO, "Data Dictionary," webpage found at http://www.imaxsoft.com/docs/99%20Other%20Manuals/03%20IMAXSOFT%20Other%20Products/DOOR/DOOR%20V1_0/PDF/Facets%20Doc/FACETS/SA_REF.PDF; Facets Data Dictionary User Guide, Release 2.8. Dec. 1998. 73 pages.

Civil Action No. 1:11-cv-11260-GAO, Facets EDI 837 Outbound Claims Submission Subsystem User Guide, Release 2.8. Dec. 1998. 193 pages.

Civil Action No. 1:11-cv-11260-GAO, Facets Internet Applications Reference Guide, Release 2.8, Dec. 1998. webpage found at http://www.imaxsoft.com/docs/99%20Other%20Manuals/03%20IMAXSOFT%20Other%20Products/DOOR/DOOR%20V1_0/PDF/Facets%20Doc/FACETS/UPDATE.PDF. 74 pages.

Civil Action No. 1:11-cv-11260-GAO, Facets Product Overview, Fall 1997, webpage found at http://www.imaxsoft.com/docs/99%20Other%20Manuals/03%20IMAXSOFT%20Other%20Products/DOOR/DOOR%20V1_0/PDF/Facets%20Doc/FACETS/OVERVIEW.PDF. 42 pages.

Civil Action No. 1:11-cv-11260-GAO, Facets User Guide: System Administration Reference, webpage found at http://www.imaxsoft.com/docs/99%20Other%20Manuals/03%20IMAXSOFT%20Other%20Products/DOOR/DOOR%20V1_0/PDF/Facets%20Doc/FACETS/INTERNET.PDF. 134 pages.

Civil Action No. 1:11-cv-11260-GAO, Facets User Guide: System Administration Processing, webpage found at http://www.imaxsoft.com/docs/99%20Other%20Manuals/03%20IMAXSOFT%20Other%20Products/DOOR/DOOR%20V1_0/PDF/Facets%20Doc/FACETS/INTERNET.PDF. 306 pages.

Civil Action No. 1:11-cv-11260-GAO, Facets Product Update, Release 2.81, Mar. 1999, webpage found at http://www.imaxsoft.

(56) References Cited

OTHER PUBLICATIONS com/docs/99%20Other%20Manuals/03%20IMAXSOFT%20Other%20Products/DOOR/DOOR%20V1_0/PDF/Facets%20Doc/FACETS/EDI8370.PDF. 394 pages.

Civil Action No. 1:11-cv-11260-GAO, Claimsnet.com Form 424B1, filed Apr. 8, 1999. 88 pages.

Civil Action No. 1:11-cv-11260-GAO, "Brochures," including all Brochure Index Links, http://web.archive.org/web/19980112180618/http://www.claimsnet.com/brochures/default.htm. 15 pages.

Civil Action No. 1:11-cv-11260-GAO, Medical Manager Corp. 1998 10-K, filed Mar. 23, 1999. 113 pages.

Civil Action No. 1:11-cv-11260-GAO, "Halley Exchange Demo Software," webpage found at http://web.archive.org/web/19971008140858/http://www.halley.com/intface.htm ("Halley Demo"). 5 pages.

Civil Action No. 1:11-cv-11260-GAO, "Halley Generated Reporting," (Complete Sample Reports), webpage found at http://web.archive.org/web/19971008140908/http://www.halley.com/hrept5.htm. 25 pages.

Civil Action No. 1:11-cv-11260-GAO, "Halley Exchange Demo Software," webpage found at http://web.archive.org/web/19971008140858/http://www.halley.com/intface.htm. (Native format). 1 page.

Civil Action No. 1:11-cv-11260-GAO, "Halley Reporting," webpage found at http://web.archive.org/web/19971008140908/http://www.halley.com/hrept5.htm. 2 pages.

Civil Action No. 1:11-cv-11260-GAO, "Halley Interface," webpage found at http://web.archive.org/web/19971008140858/http://www.halley.com/intface.htm. 4 pages.

Civil Action No. 1:11-cv-11260-GAO, "Halley Homepage," webpage found at http://web.archive.org/web/19971008140814/http://www.halley.com/. 2 pages.

Civil Action No. 1:11-cv-11260-GAO, "Halley Overview," webpage found at http://web.archive.org/web/19971008140840/http://www.halley.com/overview.htm. 2 pages.

Civil Action No. 1:11-cv-11260-GAO, "Halley Exchanges," vol. 2, Winter 1996-1997, webpage found at http://web.archive.org/web/19971008141453/http://www.halley.com/nlett2.htm . 5 pages.

Civil Action No. 1:11-cv-11260-GAO, "Halley Reasons," webpage found at http://web.archive.org/web/19971008140848/http://www.halley.com/reason.htm . 2 pages.

Civil Action No. 1:11-cv-11260-GAO, Medicode, Inc.'s Amendment No. 2 to Form S-1, filed Nov. 18, 1997 ("Medicode 1997 S-1/A"). 133 pages.

Civil Action No. 1:11-cv-11260-GAO, "Medicode Overview," http://web.archive.org/web/19980626131906/http://www.medicode.com/html/aboutmedicode.html. 3 pages.

Civil Action No. 1:11-cv-11260-GAO, Webpage found at http://web.archive.org/web/19980626132238/http://www.medicode.com/index.html. 1 page.

Civil Action No. 1:11-cv-11260-GAO, "Claims Manager Overview," webpage found at http://web.archive.org/web/19980626132425/http://www.medicode.com/html/claimsmanager.html. 2 pages.

Civil Action No. 1:11-cv-11260-GAO, AFEHCT Presentation to HCFA, Jan. 14, 1997, webpage found at http://web.archive.org/web/19990202033335/http://www.afehct.org/information_library.html. 113 pages.

Civil Action No. 1:11-cv-11260-GAO, "Software Questions," webpage found at http://web.archive.org/web/19970411063248/http://www.claimsnet.com/html/claims_processor_questions.htm. 4 pages.

Civil Action No. 1:11-cv-11260-GAO, "Sample Claims," webpage found at http://web.archive.org/web/19970411063339/http://www.claimsnet.com/html/sample_claims.htm. 1 page.

Civil Action No. 1:11-cv-11260-GAO, "Medical Services," webpage found at http://web.archive.org/web/19970411062445/http://www.claimsnet.com/html/medical_services.htm. 1 page.

Civil Action No. 1:11-cv-11260-GAO, "About Claimsnet," webpage found at http://web.archive.org/web/19970411062358/http://www.claimsnet.com/html/about_american_net_claims.htm. 1 page.

Civil Action No. 1:11-cv-11260-GAO, "Steps," webpage found at http://web.archive.org/web/19970411062637/http://www.claimsnet.com/html/7_easy_steps.htm. 1 page.

Civil Action No. 1:11-cv-11260-GAO, "Demo," webpage found at http://web.archive.org/web/19970411062653/http://www.claimsnet.com/html/claims_processor_demo.htm, including all linked steps of the demo. 6 pages.

Civil Action No. 1:11-cv-11260-GAO, "Erisco Overview," webpage found at http://web.archive.org/web/19971017134753/http://www.erisco.com/prdorvw.htm. 2 pages.

Civil Action No. 1:11-cv-11260-GAO, "Questions," webpage found at http://web.archive.org/web/19970411.063301/http://www.claimsnet.com/html/claimsnet.com_questions.htm. 3 pages.

Civil Action No. 1:11-cv-11260-GAO, Health Data Directory. Bill Briggs ed. Faulkner & Gray 2000 ed. 1999. 212 pages.

Civil Action No. 1:11-cv-11260-GAO, "Electronic Claims," http://web.archive.org/web/20000303032008/http://www.accumedic.com/ele.htm . 1 page.

Civil Action No. 1:11-cv-11260-GAO, "HCIS Products," http://web.archive.org/web/20000301143435/http://www.hcis.com/products/index.htm. 3 pages.

Civil Action No. 1:11-cv-11260-GAO, Webpage found at http://web.archive.org/web/20000303084813/http://www.accumedic.com/index.htm. 1 page.

Civil Action No. 1:11-cv-11260-GAO, Webpage found at http://web.archive.org/web/20000517042344/http://www.hcis.com/index.htm. 1 page.

Civil Action No. 1:11-cv-11260-GAO, "VISION HomeCare Overview," Webpage found at ttp://web.archive.org/web/20000523231231/http://www.hcis.com/products/vision_descrip.htm. 2 pages.

Civil Action No. 1:11-cv-11260-GAO, PC-ACE Users Manual HCFA 1500, Release 4.30 Aug. 1996. 2 pages.

Civil Action No. 1:11-cv-11260-GAO, TX-ACE Users Manual HCFA 1500, Release 6.0 Jan. 1996. 284 pages.

Civil Action No. 1:11-cv-11260-GAO, Core Module Manual, Release 10.04. Jan. 2001. 1083 pages.

Civil Action No. 1:11-cv-11260-GAO, MedicWare Interface Manual, Release 10.03 Jul. 2001. 39 pages.

Civil Action No. 1:11-cv-11260-GAO, Technical Services Bulletin: Service Pack 2 SP2. May 7, 2001. 5 pages.

Civil Action No. 1:11-cv-11260-GAO, New Client Assistance Manual Oct. 2000. 99 pages.

Civil Action No. 1:11-cv-11260-GAO, ClickON Technology Brochure. 2 pages.

\* cited by examiner

METHODS AND APPARATUS FOR GEOGRAPHY-BASED ANTIMICROBIAL RESISTANCE TRACKING

BACKGROUND

Antimicrobial agents such as antibiotics are used to treat patients who have infectious diseases. The widespread and repeated use of these agents has resulted in the adaptation of some infectious organisms to antibiotics making them less effective. It has been shown that patients with antimicrobial-resistant organisms are more likely to have extended hospital stays, thereby increasing healthcare costs, and may be at higher risk to die as a result of an infection. When a preferred antibiotic does not work for treating an infection, often a second- or third-choice drug that may be less effective, more toxic, and/or more expensive may be used, resulting in less effective treatment and higher healthcare costs. In some cases, infectious organisms may become resistant to multiple antimicrobial agents, further complicating treatment.

Hospitals and other healthcare facilities are particularly sensitive to antimicrobial resistance within their facility because close contact between sick patients is common and large quantities of antimicrobial agents are used. Such facilities may track resistance trends of inpatients in the hospital in an effort to better understand and mitigate resistance trends. Outside of the hospital setting, factors such as unnecessary overprescribing of antimicrobials and the addition of antibiotics to agricultural feed may also contribute to antimicrobial resistance.

SUMMARY

Some embodiments are directed to a method of tracking antimicrobial resistance based on geography. The method comprises receiving, by an application server, a query for antimicrobial resistance information, wherein the query includes a geographic location, wherein the query is received from an application client; determining, with at least one computer processor, a geographic region based, at least in part, on the geographic location included in the query; retrieving, from at least one health information datastore in communication with the application server, antimicrobial data for biological samples collected from patients residing in the geographic region, wherein the antimicrobial data comprises information describing antimicrobial resistance of an infectious organism detected in the biological samples to at least one antimicrobial agent; and transmitting the antimicrobial data to a client device on which the client application is executing.

Some embodiments are directed to a health information system. The health information system comprises at least one health information datastore configured to store health information for a plurality of patients of a plurality of medical practices; and an application server configured to communicate with the at least one health information datastore. The application server comprises a network interface and at least one processor. The network interface is configured to receive a query for antimicrobial resistance information from a client application, wherein the query includes a geographic location. The at least one processor is programmed to determine a geographic region based, at least in part, on the geographic location included in the query; retrieve, from the at least one health information datastore, antimicrobial data for biological samples collected from patients residing in the geographic region, wherein the antimicrobial data comprises information describing antimicrobial resistance of an infectious organism detected in the biological samples to at least one antimicrobial agent; and transmit the antimicrobial data to a client device on which the client application is executing.

Some embodiments are directed to at least one non-transitory computer-readable storage medium encoded with a plurality of instructions that, when executed by at least one computer perform a method of tracking antimicrobial resistance based on geography. The method comprises receiving, by an application server, a query for antimicrobial resistance information, wherein the query includes a geographic location, wherein the query is received from an application client; determining a geographic region based, at least in part, on the geographic location included in the query; retrieving, from at least one health information datastore in communication with the application server, antimicrobial data for biological samples collected from patients residing in the geographic region, wherein the antimicrobial data comprises information describing antimicrobial resistance of an infectious organism detected in the biological samples to at least one antimicrobial agent; and transmitting the antimicrobial data to a client device on which the client application is executing.

It should be appreciated that any combination of the foregoing concepts and additional concepts discussed in greater detail below (provided that such concepts are not mutually inconsistent) are contemplated as being part of the inventive subject matter disclosed herein.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

The present disclosure generally relates to inventive methods and apparatus for tracking antimicrobial resistance using geographic-specific information about the proportions and susceptibility of microorganisms for particular infections. Community-based healthcare providers are often limited in their access to information about antimicrobial resistance trends in their community. Lacking this information, healthcare providers often prescribe broad-spectrum antibiotics, such as fluoroquinolones, in cases where a more targeted antibiotic may be as effective. Overprescription of antimicrobial agents in general, and broad-spectrum agents in particular, exacerbates antimicrobial resistance within communities. Providing community-based healthcare providers with information about antimicrobial resistance in their geographic area may enable them to make informed decisions about prescribing antimicrobial agents to treat infectious diseases. Such informed decisions may allow for the more prudent use of antibiotics, which benefits both patients and the healthcare system.

As discussed above, some large healthcare facilities such as hospitals track antimicrobial resistance for inpatients within their facilities in an effort to mitigate the spread of antimicrobial resistance among their patients. However, information about antimicrobial resistance is not typically available outside of the hospital setting and hospitals often choose not to make this information available to the general public. Additionally, healthcare facilities often store information about antimicrobial agent usage and drug resistance in health records systems that are restrictive in their abilities to share and/or aggregate such information across multiple systems, thereby limiting the ability to track antimicrobial resistance relevant to specific geographic areas.

The inventors have recognized and appreciated that conventional systems for tracking antimicrobial resistance for inpatients in hospitals do not scale well when community-based antimicrobial resistance tracking is desired. To provide antimicrobial resistance information to healthcare providers at a regional/community level, a system that collects and/or aggregates data from patients residing in specific geographic regions is needed. Accordingly, some embodiments are directed to leveraging health information from a healthcare information system that stores patient data for medical practices located in different geographic areas. The health information stored using network-connected (e.g., cloud-based) storage may be processed and provided to community-based healthcare providers allowing them to view up-to-date information about antimicrobial resistance in their community. To this end, some embodiments are configured to retrieve antimicrobial data from large sets of health information stored in the cloud to provide geographic-specific antimicrobial resistance information to healthcare providers. Such information will enable healthcare providers to identify common and uncommon microorganisms in the communities where their patients live, and may facilitate a determination of effective treatment plans for the patients of the healthcare providers.

As discussed in more detail below, information useful for determining antimicrobial resistance trends in a particular geographic area may be available in patient's electronic medical records stored on one or more network-accessible datastores. For example, patients presenting with symptoms of a bacterial infection often provide blood, urine, or other samples to a healthcare provider for laboratory analysis to confirm a diagnosis and to help with determining an appropriate course of treatment for the infection. The results of such laboratory tests may be stored in the patient's medical record for future reference.

Patients also provide biological samples to healthcare providers for a variety of other purposes including, but not limited to, blood donation, clinical research studies, and inpatient and outpatient visits to a medical facility. An analysis of some or all of these samples may be stored in a patient's medical record and/or may be associated with a health information system (e.g., a research-based system). A medical record for a patient may be stored in any suitable way. For example, a medical record may be stored using a single system or stored across multiple systems, and the manner in which the medical record is stored does not limit the techniques described herein for providing information about antimicrobial resistance.

Laboratories, whether affiliated with a particular medical facility or not, process hundreds or thousands of samples daily, and report the sample analysis results including information on antimicrobial resistance to healthcare providers using a variety of electronic and paper-based techniques, as discussed in further detail below. Provided that the information is stored on network-accessible storage, any or all of this information about antimicrobial resistance may be used to provide community-based antimicrobial resistance information to healthcare providers in accordance with some embodiments, as discussed in further detail below.

Figure 1:
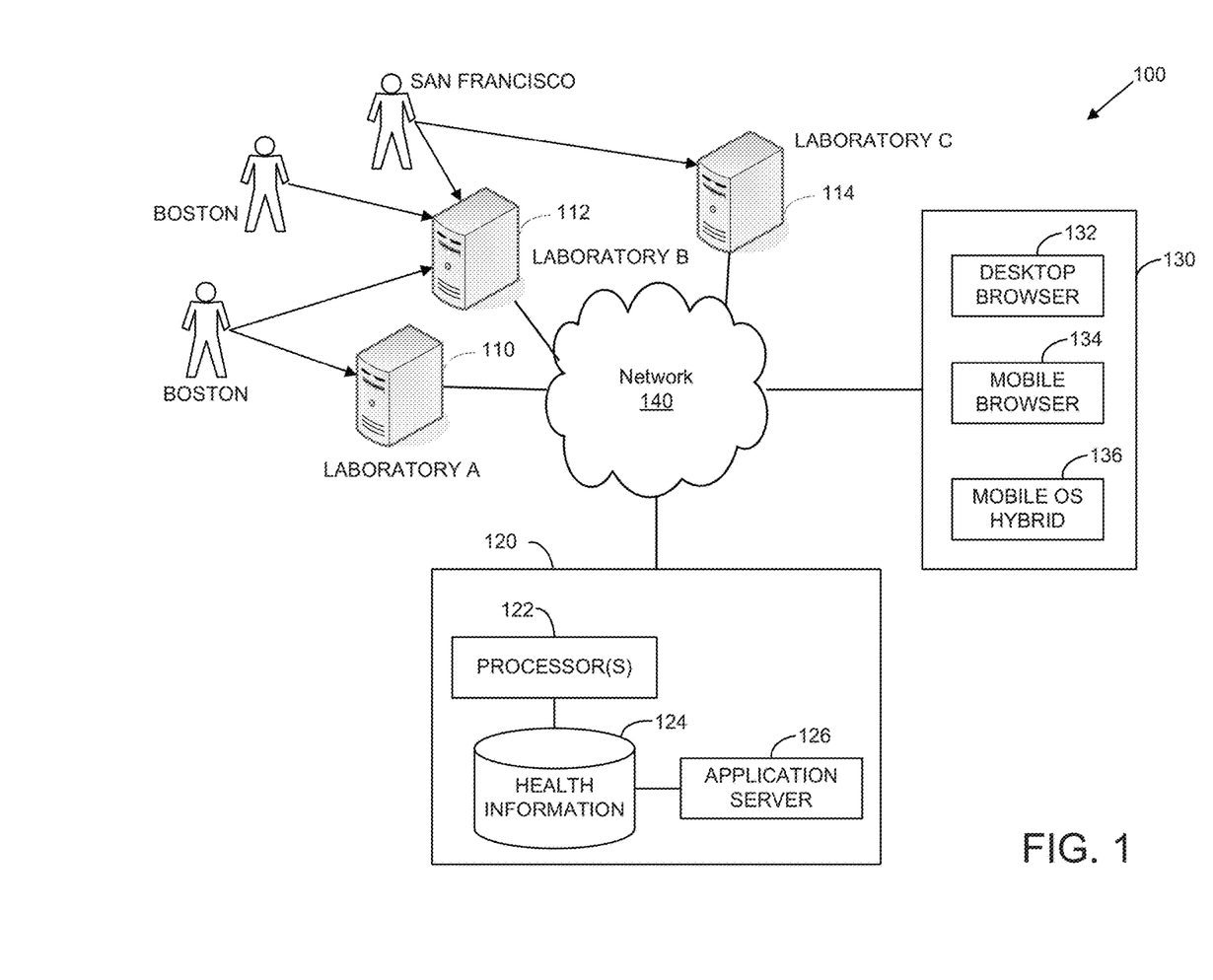
FIG. 1 is a schematic of a computing system environment within which some embodiments may be used.

FIG. 1 illustrates a system 100 for tracking antimicrobial resistance in accordance with some embodiments. System 100 includes a plurality of laboratories (e.g., laboratories 110, 112, 114), each of which processes biological specimens such as blood, urine, and skin samples, to identify infectious organisms in the specimen and to determine whether the identified infectious organisms demonstrate resistance to particular antimicrobial agents. As used herein the term "antimicrobial" refers to any agent used to eradicate, slow down, or otherwise treat an infectious organism. Examples of antimicrobial agents include, but are not limited to, antibiotics, antivirals, antifungals, antibacterials, and antiparasitics.

Samples processed by a laboratory may be associated with patients residing in different geographic locations. For example, as shown in FIG. 1, laboratory A receives samples from a patient residing in Boston, laboratory C receives samples from a patient residing in San Francisco, and laboratory B receives samples from patients residing in Boston and San Francisco. As discussed in more detail below, geographic information for a patient (e.g., the patient's home address, zip code, etc.) associated with a processed sample may be used to aggregate sample information for determining patterns of antimicrobial resistance.

After processing one or more specimens, a laboratory may generate a report including which infectious organisms were detected and information about their antimicrobial resistance. The report may be communicated to the patient's healthcare provider, where information in the report is stored by a health information system 120 used by the healthcare provider. For example, information in the report may be stored in health information datastore 124 associated with the health information system.

Laboratory reports including the results of specimen analysis may be transmitted to the health information system 120 in any suitable way. In some embodiments, laboratory reports may be transferred to health information system 120 via facsimile or by using a paper-based transfer of the information. Additionally or alternatively, laboratory reports may be electronically transmitted via network 140 to health information system 120 by electronic mail or by using a healthcare data interface configured to transfer electronic data between one or more computers at the laboratory and health information system 120. In some embodiments a healthcare data interface may be configured to ensure that electronic data sent from a laboratory's data management system (e.g., a Laboratory Information Management System (LIMS)) to the health information system 120 is appropriately mapped to data fields in or more databases (e.g., health information datastore 124) associated with the health information system 120.

Health information system 120 may include any suitable hardware and software components configured to store health information for patients of one or more healthcare providers and/or medical practices. In some embodiments, health information system 120 is a component of a web-based practice management system configured to store health information for a plurality of patients of healthcare providers at a plurality of medical practices. In such embodiments, health information system 120 may be configured to store electronic health records (EHRs) including healthcare data for the patients of the medical practices, wherein the medical practices have contracted with the provider of the practice management system to use the health information component for storing patient medical records. All or a portion of a laboratory report received from a laboratory may be stored in the patient's EHR on health information data store 124 and/or information associated with the laboratory report may be stored in any other suitable way.

As shown, health information system 120 includes one or more processors 122 arranged to access patient health information stored on health information datastore 124. Processor(s) 122 may be programmed to perform any suitable task involving health information for patients of a medical practice. For example, as discussed above, a medical practice may contract with a provider of a practice management system to use health information system 120 to store medical records (e.g., electronic health records) for patients of the medical practice. Processor(s) 122 may be programmed to transmit to one or more client computers at the medical practice, a user interface that enables the client computer(s) to access the medical records for patients of the medical practice. Authorized personnel at the medical practice may interact with the user interface displayed on the client computer(s) to retrieve data from and/or enter new information into patient medical records stored by the health information system. Processor(s) 122 may be programmed to provide any other suitable functionality to facilitate the administration of healthcare services to patients of a medical practice, and embodiments are not limited in this respect.

In some embodiments, health information system 120 is configured to store health information for patients from geographically-disparate areas. For example, health information system 120 may be implemented as a network-connected system used by a plurality of medical practices located in different parts of a state, region, country, and/or the world. The inventors have recognized and appreciated that at least some of the health information stored by such a health information system provides a rich data source that can be leveraged to provide useful information for tracking antimicrobial resistance in communities in which patients of the medical practices using the health information system reside. Accordingly, some embodiments are directed to a client/server computer architecture that aggregates and/or analyzes antimicrobial resistance data stored in a network-connected health information system to provide healthcare providers and/or other users with geographic-specific information about antimicrobial resistance trends in local communities, as discussed in more detail below.

As shown, health information system 120 includes application server 126 configured to access health information stored on health information datastore 124 and one or more client applications 130 configured to communicate with application server 126 over network 140 to receive information about antimicrobial resistance, as discussed in further detail below. Illustrative client applications 130 include, but are not limited to, desktop browsers 132, such as Internet Explorer, Firefox, Chrome, and Safari, mobile browsers 134, such as Internet Explorer Mobile, Firefox for Mobile, Chrome, and Safari, and mobile OS hybrid client applications 136. Examples of mobile OS hybrid client applications include, but are not limited to, clients for the iOS operating system provided by Apple, Inc., and clients for the Android operating system provided by Google, Inc. Mobile hybrid clients may, for example, present the antimicrobial data provided from application server 126, while also providing access to native functionality of a mobile device, including, but not limited to, global positioning system (GPS) functionality.

As discussed in more detail below, some embodiments are directed to providing antimicrobial resistance information to a client application in response to a request from the client application to provide the information. In some embodiments, the process of providing antimicrobial resistance information to client applications may be accelerated by aggregating antimicrobial data stored on health information system 120 prior to receiving a request for antimicrobial information for a particular geographic area. It should be appreciated, however, that not all embodiments require data aggregation prior to receiving a request from a client application for antimicrobial information, and embodiments are not limited in this respect.

In some embodiments, application server 126 includes one or more processors programmed to aggregate antimicrobial data stored on health information datastore 124. The antimicrobial data may be aggregated using any suitable criteria. In some embodiments, antimicrobial data is aggregated using geographic information associated with patients. For example, a geographic identifier for a patient may be determined based on the patient's home address (e.g., city, zip code, etc.), and antimicrobial data for the patient may be associated with that geographic identifier. As discussed above, patients from the same geographic region (e.g., Boston) may have samples processed by different laboratories, and the antimicrobial data for all patients from the same geographic region may be aggregated regardless of where the sample was collected or which laboratory processed the sample. In the example of FIG. 1, both laboratories A and B are shown as processing samples collected from patients residing in Boston. In some embodiments, all antimicrobial data from patients in Boston (or any other suitable geographic region) is aggregated in accordance with the techniques described herein.

Application server 126 may be configured to aggregate all antimicrobial data stored by the health information system having a geographic identifier within a particular geographic region. In one implementation, a geographic area (e.g., a state) in which antimicrobial resistance is to be tracked may be divided into regions of any suitable size. For example, a geographic area may be divided into geographic regions using a grid having cells of any suitable dimension (e.g., five square miles). In some embodiments, a geographic area may be divided into geographic regions using administrative boundaries including, but not limited to, postal codes (e.g., zip codes) and school district boundaries. The geographic identifier associated with the stored antimicrobial data may be used to aggregate the data based on geographic regions represented by the cells of the grid.

Figure 2:
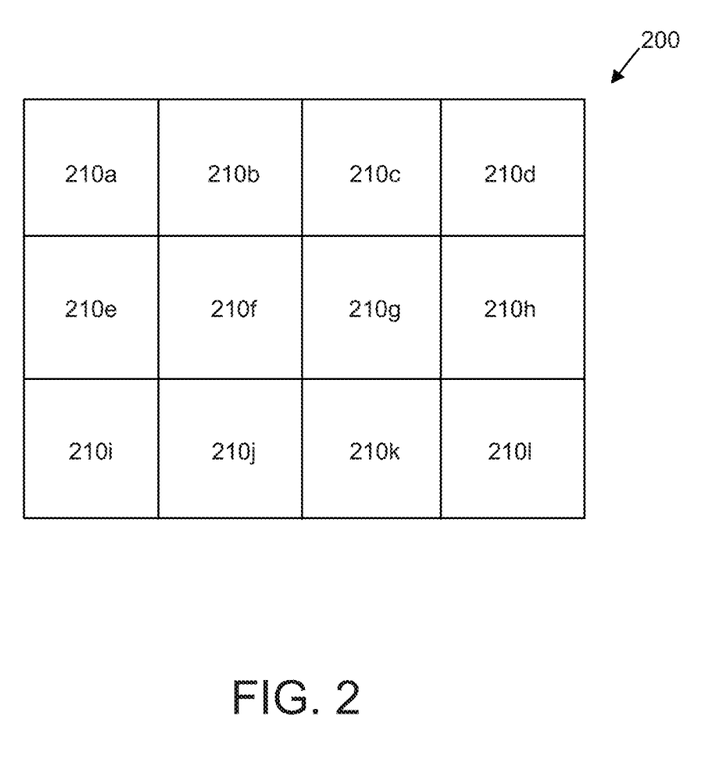
FIG. 2 is a schematic illustration of a geographic area divided into geographic regions for aggregating antimicrobial data in accordance with some embodiments.

FIG. 2 is a schematic illustration of a geographic area 200, which has been divided into twelve geographic regions identified as cells 210a-210l. Geographic area 200 is shown as being a rectangular area and the cells 210a-210l are illustrated as square geographic regions. However, it should be appreciated that a geographic area may have any shape and/or size and geographic regions within the geographic area may have any shape and/or size. For example, in some embodiments, cells may correspond to circular geographic regions having a radius of a particular dimension (e.g., five miles). In some embodiments, one or more geographic regions of a geographic area may have different shapes and/or dimensions than other geographic regions in the geographic area.

As discussed above, antimicrobial data stored by a health information system may be aggregated based, at least in part, on geographic information (e.g., all or a portion of a home address) of the patient associated with the antimicrobial data. By aggregating the data in this way, each of cells 210*a*-210*l* may be associated with a particular amount of antimicrobial data depending on the geographic distribution of the antimicrobial data stored by the health information system, and the amount of antimicrobial data associated with each cell may be used to determine a measure of the reliability of the data for that cell. Antimicrobial data associated with each cell may be stored using one or more data structures, as discussed in further detail below.

It should be appreciated that some cells may be associated with no antimicrobial data if the health information system does not store any antimicrobial data for patients associated with the geographic region corresponding to those cells. For example, geographic regions corresponding to rural areas have a lower population density, and as a result may have less patients residing therein. Accordingly, less antimicrobial data may be stored by the health information system for such sparsely-populated areas compared to more densely-populated geographic regions such as large cities.

Other factors including, but not limited to, the geographic distribution of patients having data stored by the health information system, may contribute to a particular amount of antimicrobial data being associated with a geographic region. For example, if the health information system is used primarily by medical practices serving rural areas rather than medical practices in large metropolitan areas, the amount of antimicrobial data stored for patients in rural geographic areas may be more than or the same as the amount of antimicrobial data stored for patients in large metropolitan areas, despite the rural areas having lower population densities than the large metropolitan areas.

Figure 3:
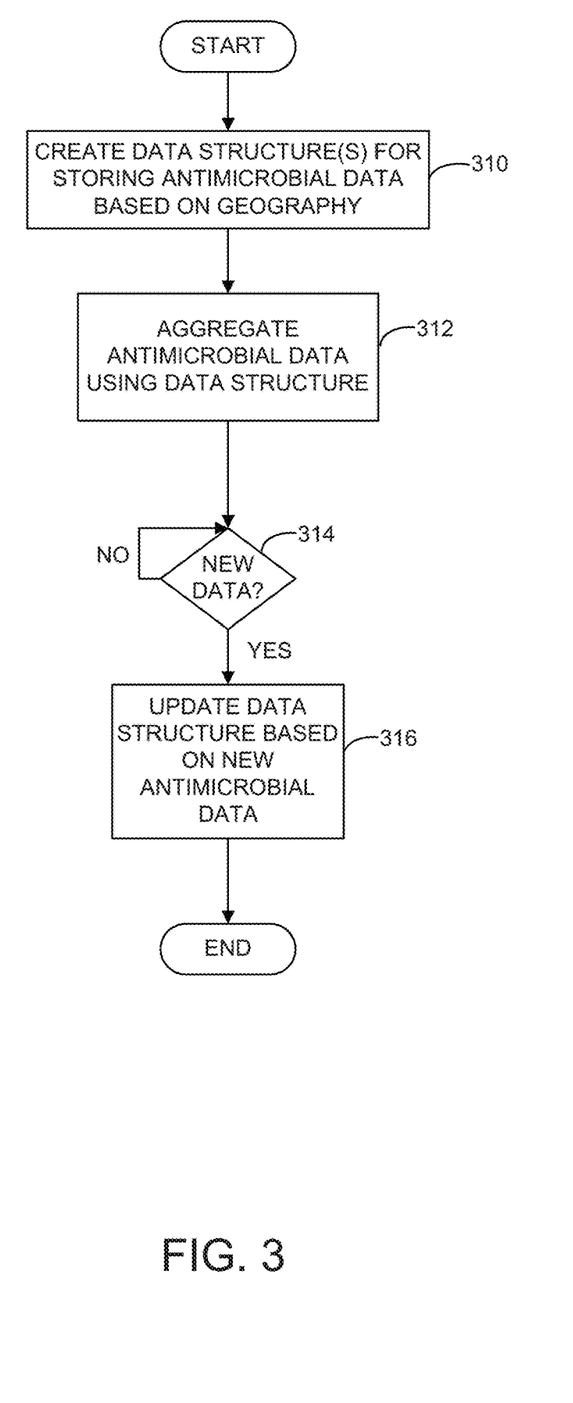
FIG. 3 is a flowchart of a process for aggregating antimicrobial data in accordance with some embodiments.

FIG. 3 illustrates a process for aggregating antimicrobial data stored in a health information system in accordance with some embodiments. In act 310, one or more data structures configured to aggregate antimicrobial data based on geographic information are created. The data structure(s) may include any suitable number of elements and sub-elements, as embodiments are not limited in this respect. In some embodiments, a data structure having a number of elements corresponding to the number of geographic regions in a geographic area may be used. Referring to the illustrative example of FIG. 2, a data structure having twelve elements may be created, wherein each of the elements of the data structure corresponds to one of the cells 210*a*-210*l*.

In some embodiments, each of the elements of the data structure comprises one or more sub-elements. For example, an element of the data structure corresponding to cell 210*a* may have sub-elements 210*a*-1, 210*a*-2, and 210*a*-3, and different antimicrobial data may be associated with each of the sub-elements. In one implementation, antimicrobial data determined from samples of different types (e.g., urine, blood, skin) are stored using different sub-elements of the data structure.

After the one or more data structures are created, the process proceeds to act 312, where antimicrobial data stored by the health information system is aggregated using the elements of the created data structure(s). The antimicrobial data may be aggregated in any suitable way. In some embodiments, antimicrobial data is stored using particular elements of a data structure based, at least in part, on geographic information associated with the antimicrobial data. For example, antimicrobial data for patients residing in a particular geographic region may be aggregated using elements of the data structure(s) corresponding to the particular geographic region, as discussed above.

In some embodiments, less than all of the antimicrobial data stored by the health information system may be aggregated. For example, in some embodiments antimicrobial data stored by the health information system may be aggregated based, at least in part, on a date and/or time associated with the antimicrobial data. For example, the date and/or time may correspond to when the sample for the antimicrobial data was collected, when the sample was processed, when the antimicrobial data was stored by the health information system, or any other suitable date and/or time associated with the antimicrobial data. In some embodiments that aggregate antimicrobial data based, at least in part, on a date and/or time associated with the antimicrobial data, antimicrobial data may only be aggregated when the date and/or time associated with the antimicrobial data falls within a particular range. For example, only antimicrobial data associated with a time within the last year, within the last month, within the last week, or within any other suitable time range may be aggregated. In some embodiments, antimicrobial data is aggregated using multiple time ranges and the aggregated data may be stored using multiple elements or sub-elements of a data structure and/or multiple data structures.

After aggregating stored antimicrobial data using the geography-based data structure(s), the process proceeds to act 314, where it is determined whether new antimicrobial data has been stored by the health information system. The determination of whether new antimicrobial data has been stored may be made in any suitable way. For example, application server 126 may include one or more processors programmed to continuously or periodically monitor when new antimicrobial data is stored by the health information system. Monitoring when new antimicrobial data is stored by the health information system may be performed in any suitable way. For example, in some embodiments, application server 126 may identify new antimicrobial data stored by the health information system based, at least in part, on one or more dates and/or times associated with the stored antimicrobial data. Additionally or alternatively, one or more components of the health information system may provide an indication to application server 126 when new antimicrobial data is stored.

If it is determined in act 314 that there is new antimicrobial data stored by the health information system, the process proceeds to act 316, where the one or more data structures created in act 310 are updated based, at least in part, on the new antimicrobial data. For example, geographic information for the new antimicrobial data may be determined, and one or more elements of the data structure(s) corresponding to the geographic information may be updated by aggregating the new antimicrobial data using those one or more elements.

If it is determined in act 314 that there is new no new antimicrobial data stored by the health information system, the process returns to act 314, where a determination of whether new data is available may be made at continuous, periodic, or aperiodic intervals until it is determined that new antimicrobial data stored by the health information system is available for aggregation. For example, the determination may be made every hour, every day, every week, or at any other suitable interval.

As discussed above, in some embodiments, antimicrobial data received from a laboratory is used to determine antimicrobial resistance of particular infectious organisms in a geographic region. The antimicrobial data describes an analysis of a sample sent to the laboratory, and is received by a health information system for storage as a report, as data formatted in a particular manner for storage by the health information system, or in any other suitable way. In some embodiments, only a subset of the information received from the laboratory may be used by application server 126 to provide antimicrobial resistance information to a client application, as discussed further below.

Figure 4:
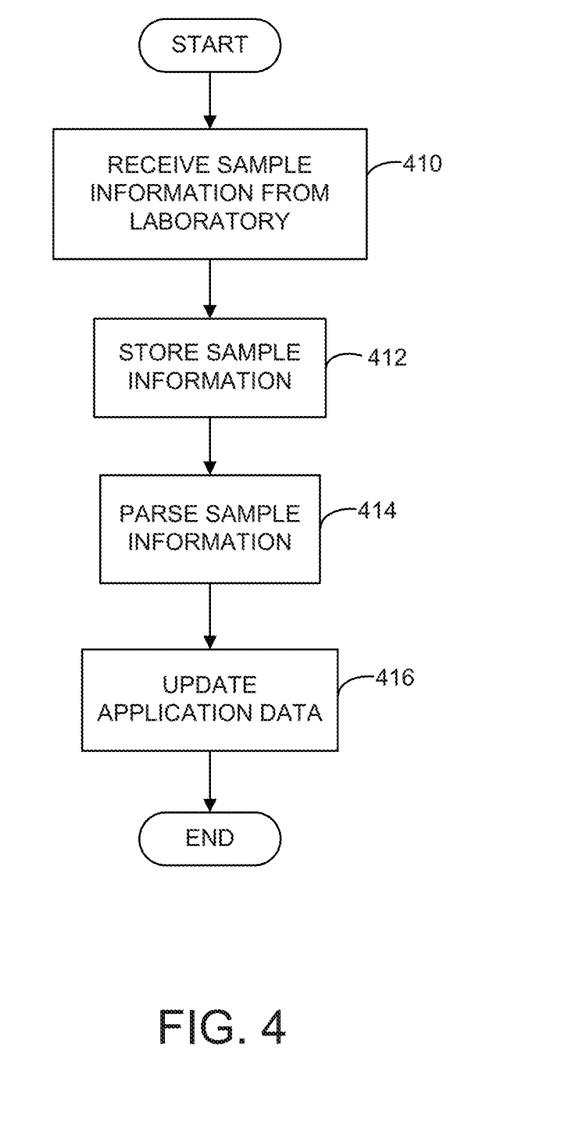
FIG. 4 is a flowchart of a process for updating a health information system with antimicrobial data received from a laboratory in accordance with some embodiments.

FIG. 4 shows a process for updating one or more components of a health information system with data used by an application server to evaluate antimicrobial resistance in accordance with some embodiments. In act 410, information describing the processing of one or more samples for a patient is received from a laboratory. The process then proceeds to act 412, where the received information is stored by the health information system. For example, a received report identifying a patient and including the antimicrobial data may be included in an electronic health record for the patient stored by the health information system. Alternatively, the received information may be stored by the health information system in any other suitable way.

The process then proceeds to act 414, where the stored information is parsed to identify antimicrobial data that may be used to track antimicrobial resistance based on a geographic identifier associated with the antimicrobial data. Any suitable antimicrobial data may be identified from the stored information, and embodiments are not limited in this respect. In some embodiments, the stored information for a processed sample is parsed to identify information including, but not limited to, the type of sample (e.g., blood, urine, skin, other), the patient associated with the sample (e.g., the patient's name or some other identifier of the patient), an indication of one or more infectious organisms identified in the sample, and information about the sensitivity of the identified infectious organism(s) to one or more antimicrobial agents (e.g., antimicrobial resistance information). Additional information about the patient associated with the sample may also be determined from the received sample information, if available. For example, geographic information associated with the patient (e.g., all or a portion of the patient's home address) may be determined if included in the received sample information.

In some embodiments, at least some information parsed from the sample information received from a laboratory may be used to identify other information stored by the health information system. For example, the sample information received from the laboratory may include a patient's name and/or some other patient identifier, but may not include an address (e.g., a home address) for the patient. The patient identifier parsed from the received sample information may be used to determine a residential address for the patient stored by the health information system. In some embodiments, even if the parsed sample information includes a residential address for the patient, this information may be used in coordination with patient information stored by one or more components of the health information system to verify the address of the patient.

After parsing the sample information, the process proceeds to act 416, where data for an antimicrobial resistance application is updated based on the parsed information and/or other information retrieved from the health information system. The application data may be updated in any suitable way including, but not limited to, the techniques described above with regard to FIG. 3 for aggregating antimicrobial data by updating one or more geographically-based data structures with antimicrobial data received from a laboratory.

Figure 5:
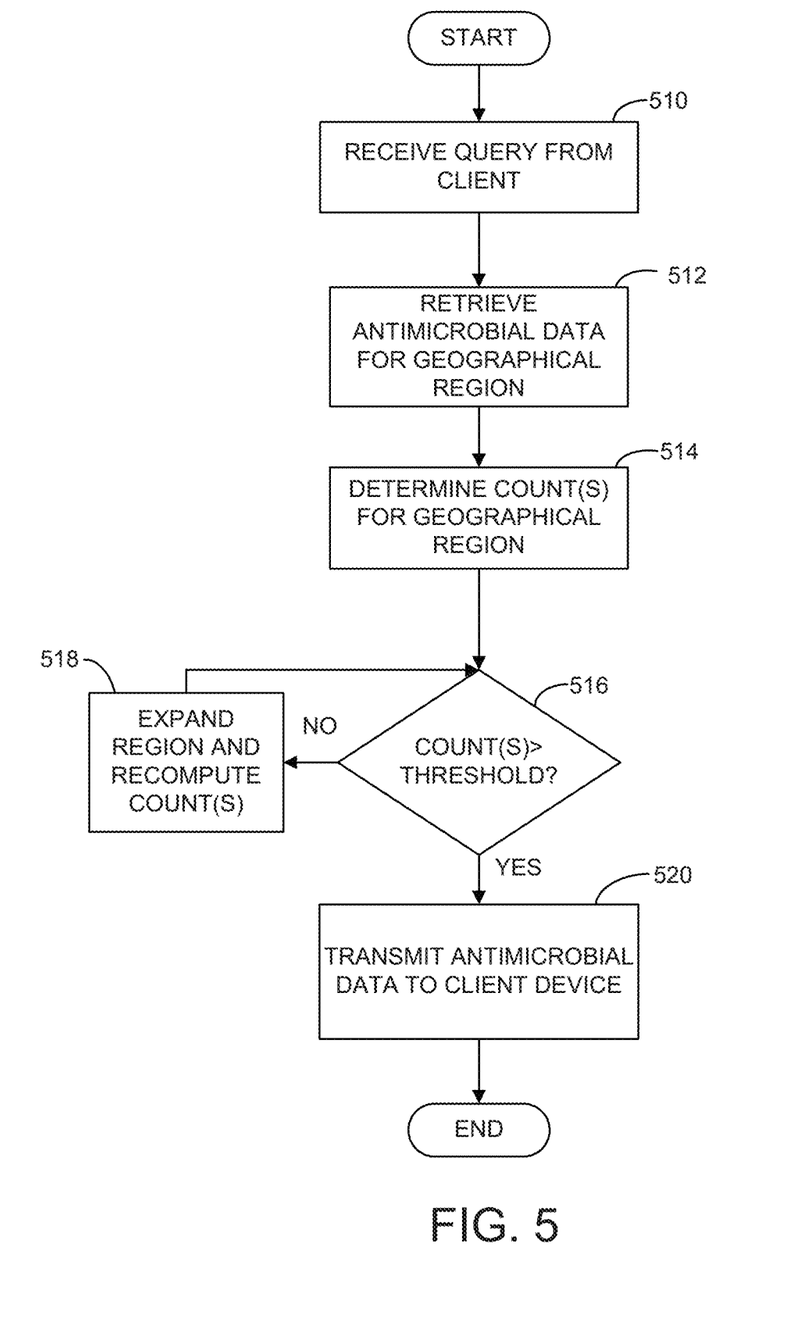
FIG. 5 is a flowchart of a process for responding to a query from a client application for antimicrobial resistance information in accordance with some embodiments.

Some embodiments are directed to a client/server computer architecture, wherein an application server includes at least one computer processor programmed to interact with one or more components of a health information system to aggregate and/or analyze antimicrobial data stored by the health information system. The application server may be configured to receive requests from a client application to provide antimicrobial resistance data for a particular geographic location, and the requested data may be transmitted to the client application in response to the query. FIG. 5 shows a process for responding to a query from a client application for antimicrobial resistance information in accordance with some embodiments.

When a user of the client application desires to retrieve antimicrobial information for a particular geographic location, the user may interact with a user interface of the client application to select one or more search parameters to transmit to the application server in a query. In act 510, the query including the one or more search parameters is received by the application server from the client application. Any suitable search parameters may be specified in the query including, but not limited to, a geographic location, a type of sample, a time window for searching, a radius for searching, a patient population of interest, and co-morbidity search parameters.

Any suitable geographic location may be included in the query including, but not limited to, a city, a county, a state, a region of a country, state, or county, a country, a zip code, a point of interest (e.g., a hospital name), and the current location of a device on which the client application is installed. For example, when the client application is installed on a mobile device such as a smartphone, the user may interact with the user interface of the client application to select "Current location" as the geographic location, and the client application may interact with a location sensor (e.g., a GPS sensor) of the mobile device to determine the current location of the mobile device. The determined current location of the mobile device may then be included in the query as a search parameter. In embodiments where a specimen type is received in the search parameters, any suitable specimen type may be used including, but not limited to urine, blood, skin, and soft tissue.

After receiving a query including search parameters from a client application, the process proceeds to act 512, where antimicrobial data are retrieved from the health information system based, at least in part, on one or more of the search parameters specified in the query. For example, antimicrobial data for biological samples of patients associated with a geographic region corresponding to the geographic location indicated in the query may be retrieved. The retrieved antimicrobial data may include information describing antimicrobial resistance of at least one infectious organism detected in the biological samples to at least one antimicrobial agent. Information about antimicrobial resistance of infectious organisms ("bugs") to antimicrobial agents ("drugs") is sometimes colloquially referred to as "bug-drug" pairs. The nomenclature of bug-drug pairs to refer to infectious organism-antimicrobial drug resistant pairs determined from laboratory samples is adopted herein for simplicity, though it should be appreciated that use of such nomenclature does not limit embodiments of the invention in any way. In some embodiments, the number of bug-drug pairs determined from samples of patients residing in a geographic region is used to assess the reliability of the antimicrobial information for that geographic region, as discussed in more detail below.

The inventors have recognized and appreciated that the reliability of antimicrobial information provided to client applications may be improved if one or more criteria are used to determine when drug resistance data for an infectious organism should be considered reliable. In some embodiments, antimicrobial data for a requested geographic region are only returned to a client application when the number of bug-drug pairs for a particular sample type within a given geographic region is greater than a threshold value. Any suitable threshold value may be used, and embodiments are not limited in this respect. For example, if the threshold value is eight hundred bug-drug pairs, the health information system must include at least eight hundred bug-drug pairs within a geographic region (e.g., a zip code) before the application server will transmit the antimicrobial data to a client application. If the geographic region does not include the required minimum number of bug-drug pairs, the geographic region may be altered (e.g., expanded) until the threshold value is reached, as discussed in more detail below. The threshold value used for each sample type may be the same or different, and embodiments are not limited in this respect.

As shown in FIG. 5, after the antimicrobial data (e.g., bug-drug pairs) is retrieved for a geographic region specified in a received query, the process proceeds to act 514, where a number of bug-drug pairs for samples of a particular specimen type for that region is determined. The process then proceeds to act 516, where it is determined whether the number of bug-drug pairs in the geographic region is greater than a threshold value. If the number of bug-drug pairs in the geographic region is less than the threshold value, the process proceeds to act 518 where the geographic region is altered. The geographic region may be altered using any suitable technique, and embodiments are not limited in this respect. In some embodiments, a size of a geographic region is gradually increased by including one or more neighboring geographic regions in latitude/longitude until the number of bug-drug pairs in the geographic region is greater than the threshold value. An example of altering a geographic region by increasing its size is discussed in more detail below.

After altering the geographic region, the process returns to act 514, where the number of bug-drug pairs in the altered geographic region is determined. The process of altering the geographic region continues until it is determined in act 516 that the number of bug-drug pairs in the geographic region is greater than or equal to the threshold value. After determining that the geographic region includes a sufficient number of bug-drug pairs, the process proceeds to act 520, where the antimicrobial data for the geographic region is transmitted to the client application that issued the query.

An example of the process of FIG. 5 is discussed in more detail below with reference to the geographic area 200 shown in FIG. 2. In this example, the application server receives a query from a client application including the following search parameters: geographic location: 210g; sample type: blood. In response to receiving this query, antimicrobial data for blood samples analyzed for patients residing in geographic region 210g are retrieved from the health information system. In this example, the reliability threshold value is set to eight hundred bug-drug pairs. Accordingly, it is determined whether the number of bug-drug pairs determined from analyzed blood samples in region 210g is greater than eight hundred. Supposing in this example that the number of retrieved bug-drug pairs determined from blood samples in region 210g is one hundred, the geographic region is increased to obtain more reliable results by including one or more of neighboring regions 210b, 210c, 210d, 210 f, 210h, 210j, 210k, and 210l. The number of bug-drug pairs in the expanded geographic region is then recomputed and if the number of bug-drug pairs is greater than threshold value, the antimicrobial information corresponding to the expanded geographic region is transmitted to the client application. In some embodiments, the antimicrobial information may be transmitted to the client application even if the threshold value of bug-drug pairs within the geographic region is not reached. In such embodiments, an indication of the reduced reliability of the antimicrobial information may be indicated by the client application.

In the process of FIG. 5, the number of bug-drug pairs for a geographic region is compared to a threshold value and the geographic region is altered based on the comparison, if necessary, in response to a receiving a query to provide the antimicrobial data. However, it should be appreciated that the bug-drug pair to threshold value comparison and geographic region altering acts of FIG. 5 (e.g., acts 514-518) may be performed at any suitable time including, but not limited to, during the data aggregation process of FIG. 3. By performing these computations prior to receiving a query from a client computer, data may be provided to requesting users more quickly than if the geographic region computations are not performed until a query is received.

In embodiments where geographic region altering is performed as part of a data aggregation process (e.g., the process of FIG. 3), determination of appropriately sized and/or shaped geographic regions based on a minimum number of bug-drug pairs in each geographic region may be performed for one or more geographic regions when updating one or more data structures based on new antimicrobial data (e.g., in act 316 of FIG. 3) in the health information system. For example, after updating the elements of a data structure to include antimicrobial information based on geographical information, the number of bug-drug pairs in some or all geographical regions represented by the data structure may be analyzed and compared to a threshold value. Based on this comparison, one or more of the geographical regions may be altered using the techniques discussed above. For example, neighboring geographical regions with numbers of bug-drug pairs below the threshold value may be grouped together to form a larger geographical region that in the aggregate has a number of bug-drug pairs greater than the threshold value. Information about the altered geographical regions may be stored on one or more storage devices accessible to the application server, and the information may be used to respond to queries from client devices requesting access to the antimicrobial data for a particular geographic location.

The antimicrobial data transmitted to the client application may include any suitable information related to antimicrobial resistance in the requested geographic location. In some embodiments, sensitivity data for one or more organisms to one or more antimicrobial agents are transmitted to the client application for display. In some embodiments, the sensitivity information may be determined as the number of isolates of an organism sensitive to the antimicrobial agent divided by the total number of isolates for the organism (e.g., sensitive, intermediate, and resistant isolates) tested for that agent in the particular geographic region of interest. In some embodiments, sensitivity data for a bug-drug pair may be indicated on a user interface of the client application. For example, antimicrobial resistance information for bug-drug pairs having greater than a particular number (e.g., thirty) of organisms tested against a given agent in the region, may be presented separately by the client application, thereby indicating the increased reliability of these results.

Figure 6A:
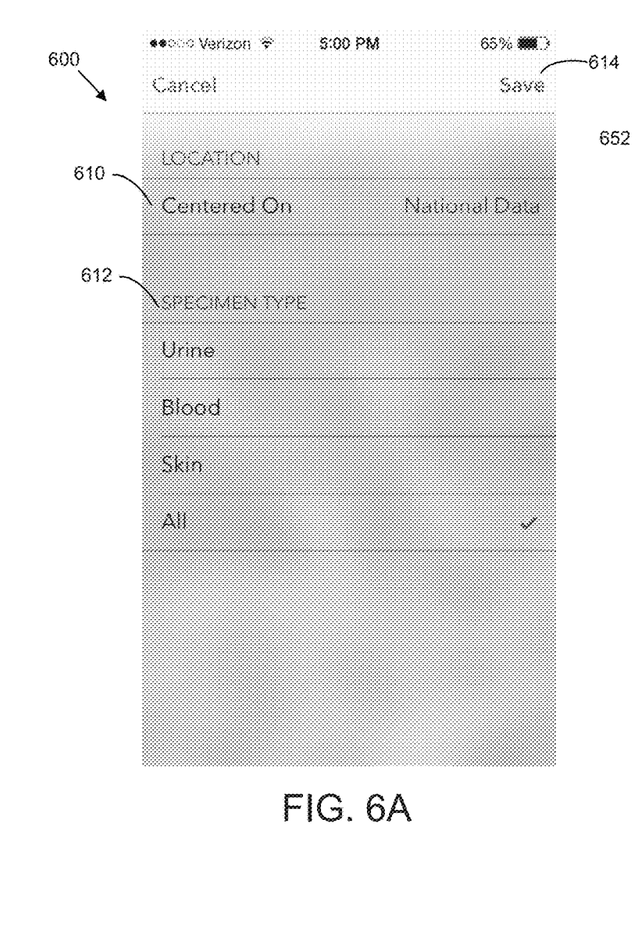
FIGS. 6A and 6B illustrate respective portions of a client application user interface for searching and displaying results of a search for antimicrobial resistance information in accordance with some embodiments.

FIG. 6A shows a search screen 600 of a user interface for a client application that may be used in accordance with some embodiments. The search screen 600 enables a user of the client application to specify search parameters for a query. For example, the search screen includes a geographic location selector 610, with which the user can interact to select a geographic location. As shown, the user has selected "National Data," which is a geographic region corresponding to a country (e.g., the United States). The search screen also includes specimen type selector 612, with which the user can interact to select a specimen type of interest. As shown, "All" has been selected indicating that the user is interested in viewing Nationwide antimicrobial resistance information for all specimen types. After the user has selected the search parameters, the user may interact with save selector 614 to transmit the query with the selected search parameters to the application server, as discussed above.

Figure 6B:
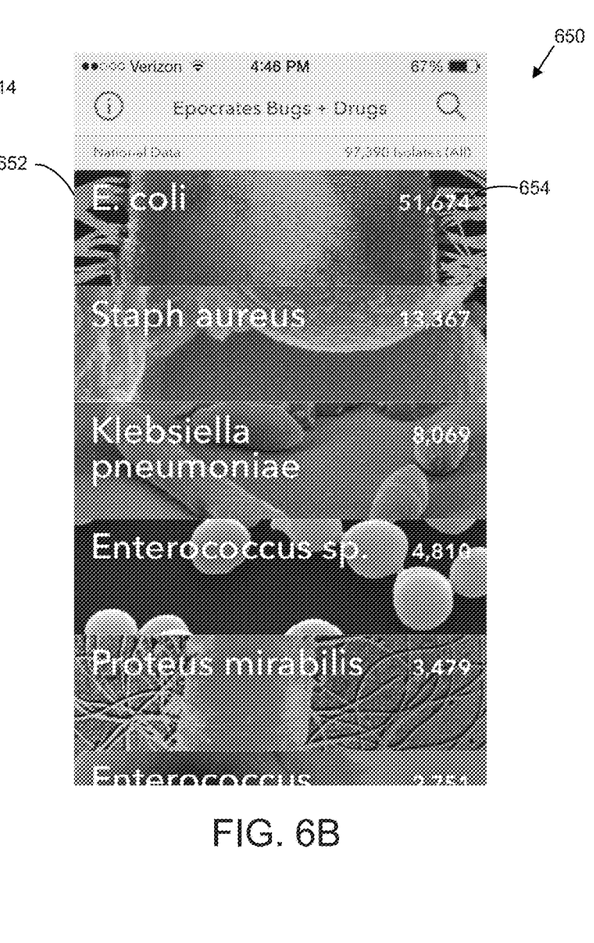

FIG. 6B shows a results screen 650 of a user interface for a client application that may be used in accordance with some embodiments. The results shown on results screen 650 correspond to antimicrobial data received by the client application in response to a query having the search parameters shown on search screen 600. Results screen 650 provides a list of organisms 652 and a number of isolates 654 for each organism in the requested geographic area, which is the United States, in this example. Other information may also be provided on results screen 650, and embodiments are not limited in this respect.

Figure 7A:
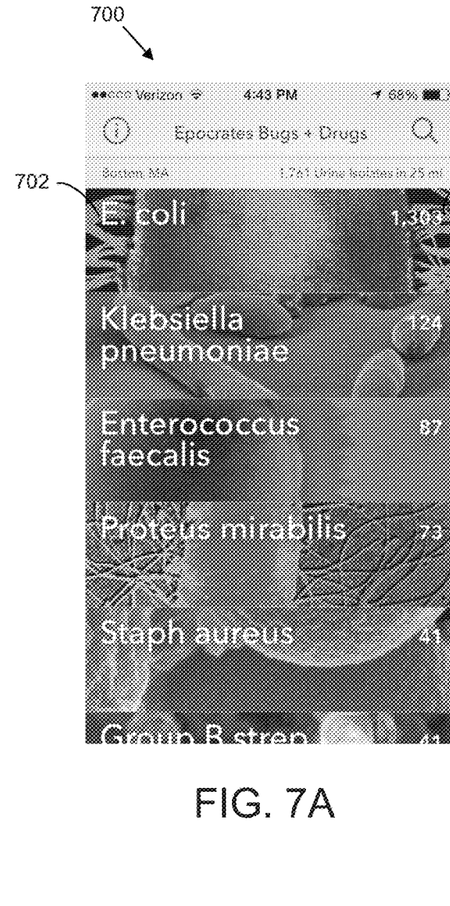
FIGS. 7A-7C illustrate portions of a client application user interface for displaying antimicrobial resistance information in accordance with some embodiments.
Figure 7B:
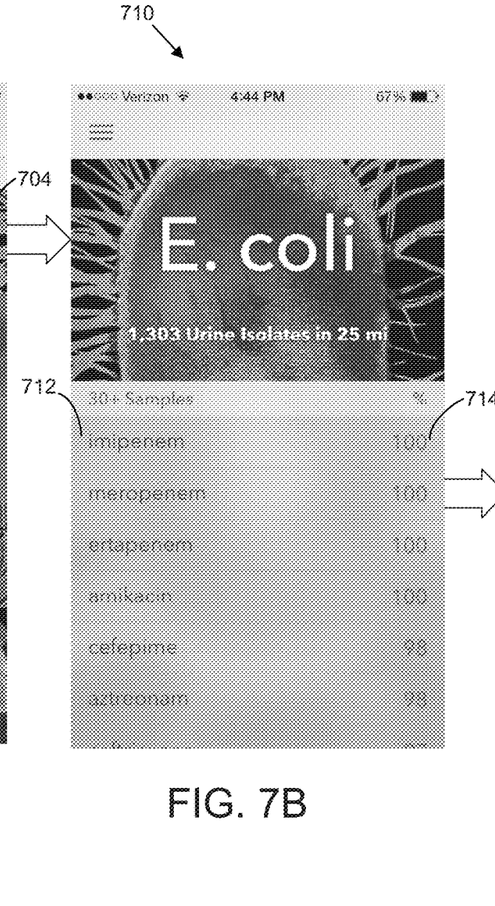
Figure 7C:
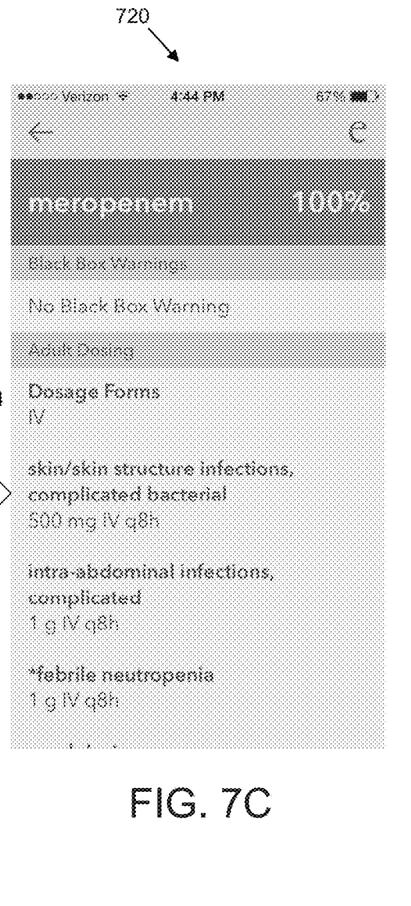

FIGS. 7A-7C show additional results screens of a user interface for a client application that may be used in accordance with some embodiments. FIG. 7A shows a results screen 700 similar to results screen 650 shown in FIG. 6B, discussed above. Results screen 700 shows results returned in response to a query having the following search parameters: geographic location: Boston, Mass.; sample type: Urine. Results screen 700 shows a list of infectious organisms 702 and a corresponding number of urine isolates 704 tested for that organism within the geographic location of Boston, Mass.

In some embodiments, a user may interact with results screen 700 to view additional detail about the results revealing more information about antimicrobial resistance in the selected geographic location. For example, in response to interacting with the "E. Coli" portion of results screen 700, the client application may show organism results screen 710, as shown in FIG. 7B. As shown, organism results screen 710 includes detailed information about the urine isolates of the E. Coli organism in the Boston, Mass. region. In particular, organism results screen 710 displays a list of antimicrobial agents 712 for which the E. Coli isolates were tested for sensitivity.

For each of the antimicrobial agents, a sensitivity measure 714 is also displayed. As shown, sensitivity measure 714 indicates a percentage of isolates for an organism that were sensitive to the antimicrobial agent. For example, 100% of urine E. Coli isolates tested in the Boston, Mass. geographic region were found to be sensitive to the antimicrobial agent imipenem, whereas only 98% of urine E. Coli isolates were found to be sensitive to the antimicrobial agent aztreonam. As discussed above, any suitable sensitivity measure may be calculated and displayed, and the sensitivity measure shown on organism results screen 710 is provided merely for illustration. For example, in some embodiments, a measure of resistance (e.g., number of resistant isolates divided by number of total isolates) rather than a measure of sensitivity may be displayed. Additionally, the reliability of the antimicrobial data displayed on organisms result screen 710 may be shown by separately displaying bug-drug pairs having more than a threshold value (e.g., thirty) of bug-drug pairs tested in the geographic region, as discussed above.

In some embodiments, one or more portions of organism results screen 710 may be interactive such that a user may interact with the portion(s) of the screen to reveal additional information about one or more of the antimicrobial agents listed on the organism results screen 710. For example, in response to interacting with the "meropenem" portion of organism results screen 710, the client application may show antimicrobial agent information screen 720, as shown in FIG. 7C. As shown, antimicrobial agent information screen 720 includes detailed information about the antimicrobial agent meropenem. The information may provide useful information about the antimicrobial agent, which a healthcare provider can use, at least in part, to make informed treatment decisions for treating patients from the patient's residential location.

The above-described embodiments can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above.

In this respect, it should be appreciated that one implementation of the techniques described herein comprises at least one non-transitory computer-readable storage medium (e.g., a computer memory, a USB drive, a flash memory, a compact disk, a tape, etc.) encoded with a computer program (i.e., a plurality of instructions) that, when executed on a processor, performs the above-discussed functions. The computer-readable storage medium can be transportable such that the program stored thereon can be loaded onto any computer resource to implement the aspects of embodiments discussed herein.

Various techniques described herein may be used alone, in combination, or in a variety of arrangements not specifically discussed in the embodiments described in the foregoing and are therefore not limited in their application to the details and arrangement of components set forth in the foregoing description or illustrated in the drawings. For example, aspects described in one embodiment may be combined in any manner with aspects described in other embodiments.

Also, embodiments may be implemented as one or more methods, of which an example has been provided. The acts performed as part of the method(s) may be ordered in any suitable way. Accordingly, embodiments may be constructed in which acts are performed in an order different than illustrated, which may include performing some acts simultaneously, even though shown as sequential acts in illustrative embodiments.

The phraseology and terminology used herein is for the purpose of description and should not be regarded as limiting. The use of "including," "comprising," "having," "containing", "involving", and variations thereof, is meant to encompass the items listed thereafter and additional items.

Having described several embodiments in detail, various modifications and improvements will readily occur to those skilled in the art. Accordingly, the foregoing description is by way of example only, and is not intended as limiting.

What is claimed is:

1. A method of tracking antimicrobial resistance based on geography, the method comprising:
    storing, on at least one health information datastore, at least one geography-based data structure, wherein the at least one geography-based data structure comprises a plurality of elements, each of the plurality of elements corresponding to a geographic area;
    receiving health information for each of a plurality of patients of a plurality of medical practices, wherein the health information includes antimicrobial data associated with a patient and a home address of the patient;
    associating the antimicrobial data with at least one of the plurality of elements of the at least one geography-based data structure, wherein the associating is performed based, at least in part, on the home address of the patient associated with the antimicrobial data;
    receiving, by an application server from a client computing device on which a client application is executing, a query for antimicrobial resistance information, wherein the query includes a geographic location;
    determining, with at least one computer processor, a geographic region based, at least in part, on the geographic location included in the query, wherein the geographic region corresponds to a larger geographic area than the geographic location; and
    retrieving, from the at least one health information datastore in communication with the application server, antimicrobial data for biological samples collected from patients having a home address in the geographic region, wherein retrieving the antimicrobial data comprises determining one or more corresponding elements of the at least one geography-based data structure which correspond to a geographic area in the determined geographic region and retrieving the antimicrobial data based, at least in part, on the one or more corresponding elements, wherein the antimicrobial data comprises:
    infectious organism-antimicrobial agent pairs, wherein each of the infectious organism-antimicrobial agent pairs corresponds to an instance of antimicrobial resistance to the antimicrobial agent in the pair of the infectious organism in the pair as detected in the biological samples;
    determining whether a number of the infectious organism-antimicrobial agent pairs specified in the retrieved antimicrobial data for the geographic region is greater than a threshold value; and
    transmitting the antimicrobial data to the client computing device in response to determining that the number of the infectious organism-antimicrobial agent pairs specified in the retrieved antimicrobial data is greater than the threshold value.

2. The method of claim 1, wherein determining the geographic region comprises:
    determining a zip code for the geographic location included in the query; and
    determining the geographic region based, at least in part, on the zip code.

3. The method of claim 1, wherein determining the geographic region comprises determining the geographic region as a region centered on the geographic location and having an area of a particular size and/or shape.

4. The method of claim 1, further comprising:
    altering, without input from the client computing device, the geographic region in response to determining that the number of the infectious organism-antimicrobial agent pairs specified in the retrieved antimicrobial data for the geographic region is less than the threshold value;
    retrieving, from the at least one health information datastore, antimicrobial data for biological samples collected from patients having a home address in the altered geographic region, wherein retrieving antimicrobial data for biological samples collected from patients having a home address in the altered geographic region comprises determining which one or more elements of the at least one data structure correspond to a geographic area in the altered geographic region and retrieving the antimicrobial data based, at least in part, on the one or more corresponding elements;
    determining whether a number of infectious organism-antimicrobial agent pairs specified in the retrieved antimicrobial data for the altered geographic region is greater than the threshold value; and
    transmitting, in response to determining that the number of infectious organism-antimicrobial agent pairs specified in the retrieved antimicrobial for the altered geographic region is greater than the threshold value, the retrieved antimicrobial data for the altered geographic region to the client device on which the client application is executing.

5. The method of claim 4, wherein altering the geographic region comprises incrementally altering a size and/or shape of the geographic region until the number of infectious organism-antimicrobial agent pairs specified in the retrieved antimicrobial data for the altered geographic region is greater than the threshold value.

6. The method of claim 4, wherein altering the geographic region comprises expanding a size of the geographic region.

7. The method of claim 1, further comprising:
    receiving an electronic laboratory report from a laboratory, wherein the electronic laboratory report includes an antimicrobial resistance analysis for one or more infectious organisms identified in at least one biological sample; and
    storing, on the at least one health information datastore, at least a portion of the antimicrobial resistance analysis for the one or more infectious organisms identified in the at least one biological sample.

8. The method of claim 7, further comprising:
    identifying a patient associated with the at least one biological sample;
    and
    updating the at least one geography-based data structure by associating at least a portion of the antimicrobial resistance analysis with at least one of the plurality of elements of the at least one geography-based data structure, wherein the associating is performed based, at least in part, on the home address of the patient.

9. The method of claim 1, further comprising:
determining based, at least in part, on the retrieved antimicrobial data, sensitivity information for each of a plurality of infectious organisms to at least one antimicrobial agent; and
transmitting the sensitivity information to the client device on which the client application is executing.

10. The method of claim 9, wherein determining the sensitivity information for each of a plurality of infectious organisms comprises:
determining a percentage of isolates for the infectious organism for the geographic region sensitive to the at least one antimicrobial agent.

11. The method of claim 1, wherein the query includes a specimen type, and wherein retrieving the antimicrobial data comprises retrieving the antimicrobial data for biological samples of a type corresponding to the specimen type included in the query.

12. The method of claim 1, wherein the query includes a specimen type, and wherein the threshold value depends, at least in part, on the specimen type included in the query.

13. The method of claim 1, wherein the antimicrobial data comprises specimen type information, wherein each of the plurality of elements of the at least one geography-based data structure includes a plurality of sub-elements, each of which corresponds to a specimen type, and wherein the method further comprises associating based, on the specimen type information, the antimicrobial data with one of the plurality of sub-elements in each of the at least one of the plurality of elements of the at least one geography-based data structure with which the antimicrobial data is associated.

14. A health information system, comprising:
at least one health information datastore configured to store health information for a plurality of patients of a plurality of medical practices, wherein the health information includes antimicrobial data associated with a patient and a home address of the patient, wherein the at least one health information datastore is further configured to store at least one geography-based data structure, wherein the at least one geography-based data structure comprises a plurality of elements, each of the plurality of elements corresponding to a geographic area, wherein one or more of the plurality of elements of the at least one geography-based data structure is associated with at least some of the antimicrobial data, wherein the associating is based, at least in part, on the home address of the patient associated with the antimicrobial data; and
an application server configured to communicate with the at least one health information datastore, wherein the application server comprises:
a network interface configured to receive a query for antimicrobial resistance information from a client application executing on a client computing device, wherein the query includes a geographic location; and
at least one processor programmed to:
determine a geographic region based, at least in part, on the geographic location included in the query, wherein the geographic region corresponds to a larger geographic area than the geographic location;
retrieve, from the at least one health information datastore, antimicrobial data for biological samples collected from patients having a home address in the geographic region, wherein retrieving the antimicrobial data comprises determining one or more corresponding elements of the at least one geography-based data structure which correspond to a geographic area in the determined geographic region and retrieving the antimicrobial data based, at least in part, on the one or more corresponding elements, wherein the antimicrobial data comprises infectious organism-antimicrobial agent pairs, wherein each of the infectious organism-antimicrobial agent pairs corresponds to an instance of antimicrobial resistance to the antimicrobial agent in the pair of the infectious organism in the pair as detected in the biological samples;
determine whether a number of the infectious organism-antimicrobial agent pairs specified in the retrieved antimicrobial data for the geographic region is greater than a threshold value; and
transmit the antimicrobial data to the client computing device in response to determining that the number of the infectious organism-antimicrobial agent pairs specified in the retrieved antimicrobial data is greater than the threshold value.

15. The health information system of claim 14, wherein the at least one health information datastore is configured to store the health information in electronic health records; and
wherein associating at least some of the antimicrobial data with one or more of the plurality of elements of the at least one geography-based data structure comprises associating the antimicrobial data from the electronic health records of all patients having a home address within the geographic area corresponding to an element of the plurality of elements, with the element.

16. The health information system of claim 14, wherein determining the geographic region comprises determining the geographic region as a region centered on the geographic location and having an area of a particular size and/or shape.

17. The health information system of claim 14, wherein the at least one processor is further programmed to:
expand a size of the geographic region in response to determining that the number of the infectious organism-antimicrobial agent pairs specified in the antimicrobial data retrieved from the at least one health information datastore is less than the threshold value; and
retrieve, from the at least one health information datastore, antimicrobial data for biological samples collected from patients having a home address in the expanded geographic region, wherein retrieving antimicrobial data for biological samples collected from patients having a home address in the expanded geographic region comprises determining which one or more elements of the at least one data structure correspond to a geographic area in the expanded geographic region and retrieving the antimicrobial data based, at least in part, on the one or more corresponding elements.

18. The health information system of claim 14, wherein the at least one processor is further programmed to:
determine based, at least in part, on the retrieved antimicrobial data, sensitivity information for each of a plurality of infectious organisms to at least one antimicrobial agent, wherein determining the sensitivity information for each of a plurality of infectious organisms comprises determining a percentage of isolates for the infectious organism for the geographic region sensitive to the at least one antimicrobial agent; and transmit the sensitivity information to the client device on which the client application is executing.

19. The health information system of claim 17, wherein the at least one processor is further programmed to:

determine whether a number of infectious organism-antimicrobial agent pairs specified in the retrieved antimicrobial data for the expanded geographic region is greater than the threshold value; and transmit, in response to determining that the number of infectious organism-antimicrobial agent pairs specified in the retrieved antimicrobial for the expanded geographic region is greater than the threshold value, the retrieved antimicrobial data for the expanded geographic region to the client device on which the client application is executing.

20. The health information system of claim 19, wherein expanding the size of the geographic region comprises incrementally expanding the size of the geographic region until the number of infectious organism-antimicrobial agent pairs specified in the retrieved antimicrobial data for the expanded geographic region is greater than the threshold value.

21. At least one non-transitory computer-readable storage medium encoded with a plurality of instructions that, when executed by at least one processor of an application server computer perform a method of tracking antimicrobial resistance based on geography, the method comprising:

storing, on at least one health information datastore, at least one geography-based data structure, wherein the at least one geography-based data structure comprises a plurality of elements, each of plurality of elements corresponding to a geographic area;

receiving health information for each of a plurality of patients of a plurality of medical practices, wherein the health information includes antimicrobial data associated with a patient and a home address of the patient;

associating the antimicrobial data with at least one of the plurality of elements of the at least one geography-based data structure, wherein the associating is performed based, at least in part, on the home address of the patient associated with the antimicrobial data;

receiving, by an application server from a client computing device on which a client application is executing, a query for antimicrobial resistance information, wherein the query includes a geographic location;

determining, with at least one computer processor, a geographic region based, at least in part, on the geographic location included in the query, wherein the geographic region corresponds to a larger geographic area than the geographic location;

retrieving, from the at least one health information datastore in communication with the application server, antimicrobial data for biological samples collected from patients having a home address in the geographic region, wherein retrieving the antimicrobial data comprises determining one or more corresponding elements of the at least one geography-based data structure which correspond to a geographic area in the determined geographic region and retrieving the antimicrobial data based, at least in part, on the one or more corresponding elements, wherein the antimicrobial data comprises infectious organism-antimicrobial agent pairs, wherein each of the infectious organism-antimicrobial agent pairs corresponds to an instance of antimicrobial resistance to the antimicrobial agent in the pair of the infectious organism in the pair as detected in the biological samples;

determining whether a number of the infectious organism-antimicrobial agent pairs specified in the retrieved antimicrobial data for the geographic region is greater than a threshold value; and transmitting the antimicrobial data to the client computing device in response to determining that the number of the infectious organism-antimicrobial agent pairs specified in the retrieved antimicrobial data is greater than the threshold value.

* * * * *